United States Patent
Liberman et al.

(10) Patent No.: US 7,977,115 B2
(45) Date of Patent: Jul. 12, 2011

(54) METHOD FOR DETERMINING COMPOSITION BALANCE OF COOLED BRINE

(75) Inventors: Barnet L. Liberman, New York, NY (US); Peter H. Glidden, Windsor, CT (US); Kevin C. Vandervoort, Suffield, CT (US); Robert J. Peacock, Lubec, ME (US)

(73) Assignee: Winterlab Limited, New York, NY (US)

(*) Notice: Subject to any disclaimer, the term of this patent is extended or adjusted under 35 U.S.C. 154(b) by 1288 days.

(21) Appl. No.: 11/095,700

(22) Filed: Mar. 31, 2005

(65) Prior Publication Data

US 2005/0166664 A1 Aug. 4, 2005

Related U.S. Application Data

(63) Continuation-in-part of application No. 10/938,081, filed on Sep. 10, 2004, now Pat. No. 7,415,832.

(60) Provisional application No. 60/515,324, filed on Oct. 29, 2003, provisional application No. 60/509,150, filed on Oct. 7, 2003.

(51) Int. Cl.
*G01N 21/00* (2006.01)

(52) U.S. Cl. ...................................................... 436/164
(58) Field of Classification Search .................. 436/164
See application file for complete search history.

(56) References Cited

U.S. PATENT DOCUMENTS

| | | | |
|---|---|---|---|
| 4,601,909 A | 7/1986 | Nagoshi | |
| 4,654,217 A | 3/1987 | Nagoshi | |
| 4,657,768 A | 4/1987 | Nagoshi | |
| 4,689,963 A | 9/1987 | Sakai | |
| 4,769,079 A * | 9/1988 | Clark et al. | 106/402 |
| 4,840,035 A * | 6/1989 | Liberman | 62/64 |
| 6,114,170 A * | 9/2000 | Habenstein | 436/2 |

* cited by examiner

*Primary Examiner* — Lore Jarrett
(74) *Attorney, Agent, or Firm* — Cohen Pontani Lieberman & Pavane LLP

(57) ABSTRACT

A method of determining whether a brine composition for freezing an item is in a desired balance. The method includes: adding an effective amount of dye into the brine composition, cooling the dye composition to a pre-determined temperature, and comparing the color of the brine composition to a pre-established correlation of color and brine composition at the pre-determined temperature, thereby determining whether the brine composition is in the desired balance.

16 Claims, 1 Drawing Sheet

METHOD FOR DETERMINING COMPOSITION BALANCE OF COOLED BRINE

CROSS REFERENCE TO RELATED APPLICATIONS

This application is a continuation-in-part of U.S. patent application Ser. No. 10/938,081 which was filed with the U.S. Patent and Trademark Office on Sep. 10, 2004, now U.S. Pat. No. 7,415,832 which claims priority from U.S. Provisional Patent Application No. 60/515,324 filed on Oct. 29, 2003 and U.S. Provisional Patent Application No. 60/509,150 filed on Oct. 7, 2003. The entire content of these related applications is herein explicitly incorporated as reference of the present application.

BACKGROUND OF THE INVENTION

1. Field of the Invention

The Present invention relates to method of determining the balance of a cooled brine composition for freezing various food products and biological samples.

2. Description of the Related Art

Methods of freezing food products for long time preservation or biological samples for cytological or histological examination are known and available. For example, liquid nitrogen is a conventional method for freezing food or biological samples. Nevertheless, this method is costly since the liquid nitrogen is expensive. Moreover, there may be damage to the cellular structure of the foods or biological samples, which in turn results in deterioration in the quality of the foods, or interferes with a rapid and accurate examination of cryogenically frozen tissue.

Using cooled brine (antifreeze solution) is another conventional freezing method. Brine includes inorganic substances such as calcium chloride, and organic substances such as ethylene glycol, and propylene glycol. Furthermore, the solution prepared by mixing the above ingredients is advantageous in that greater cooling is achieved at a comparatively lower price.

For example, "A Method of Freezing Fishery Products" is known from U.S. Pat. No. 4,601,909 issued to Nagoshi on Jul. 22, 1986. This method includes the steps of preparing a brine containing rapeseed oil, propylene glycol, calcium chloride and water, cooling the brine and immersing the seafood in the cooled brine until it is frozen. This method reduces or eliminates breakdown of muscle tissue in the seafood. Hence, deterioration in quality of the frozen product is prevented or reduced.

A similar process for "Quick Freezing of Meat" is disclosed and claimed in U.S. Pat. No. 4,654,217 issued to Nagoshi on Mar. 31, 1987. The process disclosed in this later patent is similar to that disclosed in the earlier patent except that it is applicable to beef, poultry, pork and the like.

U.S. Pat. No. 4,657,768 issued to Nagoshi on Apr. 14, 1987, discloses a "Freezing Method for Perishable Foods" which includes placing a perishable food in a heat conducting container and causing the other surface of the heat conducting container to contact cooled brine or a liquefied gas. Accordingly, the perishable food is frozen quickly without immersion.

U.S. Pat. No. 4,689,963 issued to Sakai on Sep. 1, 1987, relates to a method of freezing foods. The method of Sakai is similar to the methods of Nagoshi except that a layer of brine is placed in the heat conducting container along with the perishable food. Freezing proceeds only from the portion which is in contact with the brine and the potential for the food to stick to the container is reduced.

U.S. Pat. No. 4,840,035 provides a method of freezing a tissue specimen by using a brine comprising a cruciferous oil.

The composition of the cooled brine is an important consideration for attaining desirable freezing results. None of the aforementioned patents provides a fast, simple, and convenient in-process method of determining whether the composition of the cooled brine is in a desired balance.

SUMMARY OF THE INVENTION

It is, therefore, an object of the present invention to provide a simple, convenient, and fast method of determining whether a cooled brine composition for freezing an item such as food products and biological samples is within a desired balance.

Therefore, the present invention provides a method of determining whether a brine composition for freezing an item is of a desired balance. The method is performed by:

adding an effective amount of water soluble dye into the brine composition, cooling the brine composition to a pre-determined temperature, and comparing the color of the brine composition to a pre-established correlation of color and brine composition at the pre-determined temperature thereby determining whether the brine composition is in the desired balance.

The method may further include steps of measuring the specific gravity of the brine composition and comparing the specific gravity to a pre-established correlation of specific gravity and the brine composition. Thus, these further steps may be used to confirm the determination made in the step of comparing the color of the brine composition to the pre-established correlation of color and brine composition at the pre-determine temperature. These additional steps are preferable when the color of the brine composition indicates that the brine composition is not in the desired balance.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

DETAILED DESCRIPTION OF THE PRESENTLY PREFERRED EMBODIMENTS

Figure 1:
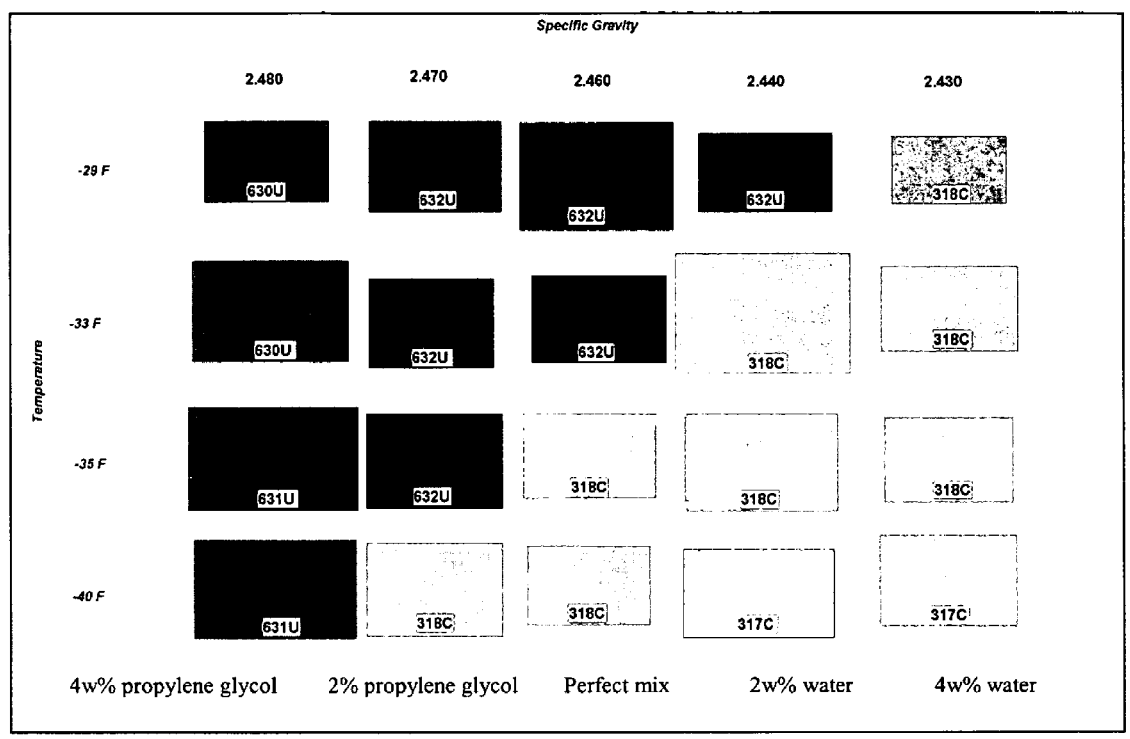
FIG. 1 is a standard color chart showing the correlation between the color and composition of a brine composition at certain temperatures.

As used herein, the term "an item" means anything that is suitable for being frozen with brine, which includes food and/or a biological sample. The food may be meat, seafood, vegetables, or fruit. The biological sample may be tissue, fertilized eggs, unfertilized eggs or the like.

The pre-established correlation of color (or specific gravity) and the brine composition is established to show different colors (or specific gravities) of a composition of a desired balance and other compositions that deviate from the desired balance. In the composition of the desired balance, each ingredient contained therein has a desired amount. In other compositions, at least one ingredient is in an amount that deviates from the desired amount. The amount of the ingredient may be in volume, weight, or ratio of one ingredient to other ingredient contained in the brine composition. For example, the amount of the ingredient may be in a weight percentage of the total amount of the brine composition. The amount of the ingredient may be expressed by the deviation degree from the desired amount. The pre-established correlation may optionally be established with respect to only one or more important ingredients instead of all the ingredients contained in the brine composition.

The pre-established correlation of color and brine composition may be shown in a standard color chart. For example, a color wheel guide may be devised to establish the perfect balance color at different temperatures, such as from −20° C. to −42° C. (−4° F. to −44° F.), preferably from −34° C. to −40° C. (−29° F. to −40° F.). Thus, if the color of a brine solution later used does not match the color at the corresponding temperature in the color wheel, it indicates that the brine solution does not have the desired composition balance. Then a further full analysis of the brine solution, such as specific gravity, may need to be performed.

The brine composition can be any composition suitable for freezing an item, such as any of the brine solutions disclosed in U.S. Pat. Nos. 4,601,909; 4,654,217; 4,657,768; 4,689,963; 4,743,343; 4,840,034; 4,840,035; 5,001,047; and 6,248,381, the contents of which patents are incorporated herein by reference in their entireties.

Preferably, the brine comprises at least about 0.005% by weight of cruciferous oil. More preferably, about 0.005% to 0.018% by weight of cruciferous oil such as rapeseed oil may be used. Alternatively, the amount of cruciferous oil may be selected such that a maximum amount of the oil is dissolved in the brine.

The brine composition preferably comprises propylene glycol and water. It is also preferable that the brine composition contains calcium chloride. The water used in the composition is preferably deionized before being added into the brine composition.

In accordance with one embodiment of the present invention, the brine composition in a desired balance comprises about 0.01% by weight of rapeseed oil, about 43.18% by weight of water, about 44.06% by weight of propylene glycol, and about 12.75% by weight of calcium chloride.

The dye is used in a sufficient amount to confer the desired distinctive color to the brine and produce distinguishable colors in different brine compositions at a pre-determined temperature. The dye may be used in an amount of from 0.000005 to 0.00004, preferably from 0.00001 to 0.00002, more preferably about 0.00001 weight percent of the brine composition.

The dye used in the present invention can be any suitable dye, which can confer a desired color to the brine and produce distinguishable color effects in connection with different brine compositions. The dye suitable used in the present invention should be water soluble.

Examples of the dye suitable in the present invention include:
1) Bright Dyes® Blue, Yellow/Green, 1 GALLON TREATS 100,000 GALLONS OF WATER;
2) TRUE BLUE™, 5.25 OUNCE TREATS 325,000 GALLONS OF WATER;
3) Neelikon Food Dyes: Neeligran FD&C Yellow 5, Neeligran FD&C Yellow 6, Neeligran FD&C Red 40, Neeligran FD&C Red 3, Neeligran FD&C Blue 2, Neeligran FD&C Blue 1, and Neeligran FD&C Green 3; and
4) COLOREZE™ FD&C Yellow 5, FD&C Yellow 6, FD&C Red 40, FD&C Red 3, FD&C Blue 2, FD&C Blue 1, and FD&C Green 3.

Preferably, the dye is a food grade FDA approved dye, with a distinctive color such as blue. One preferable dye suitable used in the present invention is Bright Dyes® Standard Blue™ liquid concentrate manufactured by Kingscote Chemicals, Inc. of Ohio.

The dye may be added into the brine composition by mixing with other substances contained in the brine composition when preparing the brine composition. Alternatively, the dye may be added into a previously prepared brine composition. The dye may be added to the brine composition before or after the brine composition is cooled to the pre-determined temperature.

The following examples further illustrate the present invention without limiting it.

Example

This Example provides a specific procedure for establishing the color chart of a brine composition. The brine composition in a desired balance comprises about 0.01% by weight of rapeseed oil, about 43.18% by weight of water, about 44.06% by weight of propylene glycol, and about 12.75% by weight of calcium chloride.

The procedure comprises:
a) mix 265 liters (70 U.S. gallons) of the brine composition in the desired balance perfectly with 2.65 ml Bright Dyes™ dye to make a colored brine;
b) place 189 liters (50 U.S. gallons) of the colored brine in a freezer;
c) prepare ten 0.946 liters (1 quart) samples of brine by respectively decreasing the water concentration of the colored brine by 2%, 6%, 10%, . . . , and 40%;
d) prepare ten 0.946 liters (1 quart) samples of brine by respectively decreasing the propylene glycol concentration of the colored brine by 2%, 4%, 6%, . . . , and 20%.
e) place samples of the off brine samples of c) and d) in a small container, open top, reduce temperature to −40° C., and stir;
f) when both good brine of b) and off brine samples of c) and d) are at the same temperature, take photos of the good brine and off brine with good overhead light;
g) make a color chart in accordance with the photos of f) showing the correlation of the color and the composition of the brine solution; and
h) repeat the above, respectively, at −34° C. (−29° F.), −36° C. (−33° F.), −37° C. (−35° F.), and −40° C. (−40° F.).

FIG. 1 is a color chart prepared in accordance with the procedure in the above Example. From the left to the right in FIG. 1, the five pictures at each temperature respectfully represent the colors of the brine compositions containing 4 w % and 2 w % more than the desired amount of propylene glycol, the composition with each ingredient in the desired amount, compositions containing 2 w % and 4 w % more than the desired amount of water. Each picture in the color chart corresponds to a pantone color value. Hence, a quantified value such as a pantone color value of the brine composition to be used may be determined and compared to a pre-established correlation of quantified color values and brine compositions.

As shown by FIG. 1, the color effects associated with different brine compositions are distinguishing. For example, at −36° C. (−33° F.), the color of the brine composition containing more than desired amount of water is sharply different from that of the brine composition in a desired balance. Likewise, at −37° C. (−35° F.), the color of the brine composition containing more than desired amount of propylene glycol is sharply different form that of the brine composition in a desired balance.

The invention is not limited by the embodiments described above which are presented as examples only but can be modified in various ways within the scope of protection defined by the appended patent claims.

We claim:

1. A method of determining whether a brine composition for freezing an item is of a desired balance comprising:
   adding an effective amount of water soluble dye to the brine composition;
   cooling the brine composition to a pre-determined temperature so that ice crystals are formed in the brine composition; and
   comparing the color of the brine composition to a pre-established correlation of color and brine composition at the pre-determined temperature thereby determining whether the brine composition is in the desired balance.

2. The method of claim 1 further comprising steps of measuring the specific gravity of the brine composition and comparing the measured specific gravity to a pre-established correlation of gravity and brine composition for further confirming the determination made in the step of comparing.

3. The method of claim 1 wherein the pre-established correlation of color and brine composition is shown in a standard color chart.

4. The method of claim 1 wherein the brine comprises propylene glycol and water.

5. The method of claim 4 wherein the water is deionized water.

6. The method of claim 1 wherein the pre-determined temperature is from −20° C. to −42° C.

7. The method of claim 1 wherein the pre-determined temperature is from −34° C. to −40° C.

8. The method of claim 1 wherein the amount of dye is from about 0.000005 to 0.00004 weight percent of the brine composition.

9. The method of claim 1 wherein the amount of dye is from about 0.00001 to about 0.00002 weight percent of the brine composition.

10. The method of claim 1 wherein the amount of dye is about 0.00001 weight percent of the composition.

11. The method of claim 1 wherein the dye is a food grade FDA approved dye.

12. The method of claim 11 wherein the food grade FDA approved dye is a blue dye.

13. The method of claim 1 wherein the brine composition comprises at least 0.005% by weight of cruciferous oil.

14. The method of claim 1 wherein the brine composition comprises rapeseed oil, water, propylene glycol, and calcium chloride.

15. The method of claim 14 wherein the brine composition in the desired balance comprises about 0.01% by weight of rapeseed oil, about 43.18% by weight of water, about 44.06% by weight of propylene glycol, and about 12.75% by weight of calcium chloride.

16. The method of claim 1 wherein the color of the brine composition is expressed by a quantified value, the pre-established correlation of color and brine composition is a correlation of quantified color value and brine composition.

* * * * *